United States Patent
Park et al.

(10) Patent No.: US 12,246,173 B2
(45) Date of Patent: Mar. 11, 2025

(54) ELECTRODE WIRE FOR APPLYING ELECTRICAL STIMULATION TO BODY ORGANS, AND ELECTRODE SYSTEM USING SAME

(71) Applicant: SAMSUNG LIFE PUBLIC WELFARE FOUNDATION, Seoul (KR)

(72) Inventors: Eun Kyoung Park, Seoul (KR); Tae Kyung Kim, Seoul (KR); Tae Woo Kim, Seoul (KR); Kyu Sung Lee, Seoul (KR)

(73) Assignee: SAMSUNG LIFE PUBLIC WELFARE FOUNDATION (KR)

( * ) Notice: Subject to any disclaimer, the term of this patent is extended or adjusted under 35 U.S.C. 154(b) by 383 days.

(21) Appl. No.: 17/921,961

(22) PCT Filed: Apr. 1, 2021

(86) PCT No.: PCT/KR2021/004087
§ 371 (c)(1),
(2) Date: Oct. 27, 2022

(87) PCT Pub. No.: WO2021/221327
PCT Pub. Date: Nov. 4, 2021

(65) Prior Publication Data
US 2023/0173260 A1    Jun. 8, 2023

(30) Foreign Application Priority Data

Apr. 28, 2020  (KR) .......................... 10-2020-0051335

(51) Int. Cl.
*A61N 1/375* (2006.01)
*A61N 1/05* (2006.01)

(52) U.S. Cl.
CPC ....... *A61N 1/0534* (2013.01); *A61N 1/37514* (2017.08)

(58) Field of Classification Search
CPC .............. A61N 1/0534; A61N 1/37514; A61N 1/0539; A61N 1/36067; A61N 1/36096; A61N 1/36125; A61N 1/36128
See application file for complete search history.

(56) References Cited

U.S. PATENT DOCUMENTS

2006/0217779 A1    9/2006  Ransbury et al.
2007/0027514 A1*   2/2007  Gerber .................... A61N 1/05
                                                              607/116

(Continued)

FOREIGN PATENT DOCUMENTS

| JP | 2007-202727 A | 8/2007 |
| KR | 10-1033749 B1 | 5/2011 |
| KR | 10-2020-0016103 A | 2/2020 |

OTHER PUBLICATIONS

International Search Report of WIPO in Application No. PCT/KR2021/004087, filed Apr. 1, 2021.

*Primary Examiner* — Ankit D Tejani
*Assistant Examiner* — Joshua Brendon Solomon
(74) *Attorney, Agent, or Firm* — Dilworth IP, LLC (57) ABSTRACT

The lead implanted in a body to apply electrical stimulation to body organs may include: an electrode wire having one end provided as an insertion portion to be inserted into a body and the other end provided as an interface portion for connection with an external device to transmit a stimulation signal: a plurality of first electrodes in the insertion portion; a plurality of second electrodes on the interface portion; and a plurality of signal lines interconnecting the first electrodes and the second electrodes, wherein the insertion portion of the electrode wire includes a plurality of support portions on which the first electrodes are respectively disposed and a (Continued)

plurality of stretchable portions between the support portions and expandable and contractible, and further includes an operation unit for pushing or pulling each support portion in a longitudinal direction of the electrode wire to adjust a position of the support portion.

6 Claims, 5 Drawing Sheets

(56) References Cited

U.S. PATENT DOCUMENTS

2010/0331938 A1   12/2010  Sommer et al.
2014/0066922 A1    3/2014  Coe et al.

* cited by examiner

ELECTRODE WIRE FOR APPLYING ELECTRICAL STIMULATION TO BODY ORGANS, AND ELECTRODE SYSTEM USING SAME

FIELD OF THE INVENTION

The present invention relates to a lead for applying electrical stimulation to body organs and a lead system using the same.

BACKGROUND OF THE INVENTION

Due to the complexity of modern society, modern people are easily exposed to accidents or diseases and lose their intrinsic functions or exercise abilities, but there is a limit to healing these patients with medicine alone. In order to overcome these limitations, the field of biomedical engineering, which was created by grafting the technology of the engineering field with the medical field, is developing, and as a result, major changes are occurring in many areas of a health care system.

For example, pacemakers and ventricular defibrillators are saving many lives and playing an innovative role in the treatment of heart disease. In addition, using pacemaker technology, the surgeon implants a Deep Brain Stimulation (DBS) device into the patient's brain to control an abnormal brain function (e.g., see patent documents).

Abnormal physical behavior or mental disorders result from abnormal functions of the brain, such as Parkinson's Disease (PD) or Obsessive-Compulsive Disorder (OCD). PD is a chronic degenerative brain disease in which the main symptoms are trembling hands and feet, slow movements, and stiff muscles, and OCD is a mental disorder in which people are reluctant to go out because of fear that they may be contaminated by things they come in contact with.

Neurosurgeons are now using deep brain stimulators to treat serious health problems such as Parkinson's disease, obsessive-compulsive disorder and depression. A treatment method using a deep brain stimulator is a surgical method, and it is the only hope for treating obsessive-compulsive disorder and is evaluated as a method that has been proven effective in curing Parkinson's disease.

Deep brain stimulation utilizes implantable medical devices to deliver accurate electric pulses. A deep brain stimulator is largely composed of an implantable pulse generator, an extension, and a lead.

It is important to check the position and contact point of a lead after surgery because the clinical course may differ for each patient depending on the position of the lead. Accordingly, during deep brain stimulation and lead implantation surgery, it is necessary to check an electrode stimulation position through various measurement methods such as MRI, CT image, C-arm image, and cranial nerve signal. However, if sufficient micro-electrical stimulation is not made to a correct target, it is difficult to expect a therapeutic effect.

However, it is by no means easy to perform re-correction surgery each time during or after surgery according to a wrong insertion position of an electrode, changes in electrode position and contact point due to physical factors, and whether or not there is a response due to stimulation in terms of the patient's quality of life or the stability of surgery and medical devices. However, the prior art does not provide a clear solution to this.

SUMMARY OF THE INVENTION

The present invention provides a lead capable of adjusting a contact point and a position of an electrode that applies electrical stimulation to body organs from the outside after the electrode is implanted in the body, and a lead system using the lead.

As an embodiment of the present disclosure, a lead may be provided.

The lead implanted in a body to apply electrical stimulation to body organs according to an embodiment of the present disclosure may include: an electrode wire having one end provided as an insertion portion to be inserted into a body and the other end provided as an interface portion for connection with an external device to transmit a stimulation signal to body organs into which the lead is inserted; a plurality of first electrodes in the insertion portion to transmit electrical stimulation to body organs; a plurality of second electrodes on the interface portion to receive electrical stimulation applied from outside; and a plurality of signal lines configured to interconnect the first electrodes and the second electrodes, respectively, and transmit the electrical stimulation received by the second electrodes to the first electrodes, wherein the insertion portion of the electrode wire comprises a plurality of support portions on which the first electrodes are respectively disposed and a plurality of stretchable portions between the support portions and expandable and contractible, and further comprises an operation unit for pushing or pulling each support portion in a longitudinal direction of the electrode wire, wherein, by pushing or pulling each support portion, a stretchable portion between the support portions is stretched and contracted to adjust a position of the support portion.

The lead according to an embodiment of the present disclosure may further include one end of a plurality of operation wires is coupled to each support portion as an operation unit and the other end of the operation wires extends to an outside of the lead, and by pushing or pulling the other end of the operation wires, a position of each support portion with respect to the electrode wire is adjusted, or an angle of arrangement of the support portion with respect to an extension direction of the electrode wire is adjusted.

The lead according to an embodiment of the present disclosure may further include a plurality of moving plates each movable in the longitudinal direction of the electrode wire are disposed on the interface portion of the electrode wire, and one end of a plurality of operation wires is coupled to each support portion as an operation unit and the other end of the operation wires is coupled to each moving plate, so that each operation wire pushes or pulls each support portion by movement of each moving plate.

As an embodiment of the present disclosure, a lead system may be provided.

The lead system implanted in a body to apply electrical stimulation to body organs according to an embodiment of the present disclosure may include: a main processor connected to an external device for communication and control; one or more leads implanted in a body to apply electrical stimulation to body organs; an electrode clamp for electrical connection with a lead; and a controller for controlling a position of transmitting electrical stimulation in the lead, wherein each lead comprises: an electrode wire having one end provided as an insertion portion to be inserted into a body and the other end provided as an interface portion for connection with an external device to transmit a stimulation signal to body organs into which the lead is inserted; a plurality of first electrodes in the insertion portion to transmit electrical stimulation to body organs; a plurality of second electrodes on the interface portion to receive electrical stimulation applied from outside; and a plurality of signal lines configured to interconnect the first electrodes and the second electrodes, respectively, and transmit the electrical stimulation received by the second electrodes to the first electrodes, wherein the insertion portion of the electrode wire comprises a plurality of support portions on which the first electrodes are respectively disposed and a plurality of stretchable portions between the support portions and expandable and contractible, and further comprises an operation unit for pushing or pulling each support portion in a longitudinal direction of the electrode wire, wherein, by pushing or pulling each support portion, a stretchable portion between the support portions is stretched and contracted to adjust a position of the support portion.

The lead system according to an embodiment of the present disclosure may further include a plurality of operation wires are coupled as an operation unit to each support portion of the lead, and a position of each support portion with respect to the electrode wire is adjusted by pushing or pulling the operation wires, or an angle of arrangement of the support portion with respect to an extension direction of the electrode wire is adjusted, wherein the controller comprises a motor that pushes or pulls each operation wire of the lead.

The lead system according to an embodiment of the present disclosure may further include a plurality of moving plates each movable in the longitudinal direction of the electrode wire are disposed on the interface portion of the electrode wire, and one end of a plurality of operation wires is coupled to each support portion as an operation unit and the other end of the operation wires is coupled to each moving plate, so that each operation wire pushes or pulls each support portion by movement of each moving plate, wherein the controller is provided with an actuator coupled with each moving plate of the lead to move the moving plate.

According to the present invention, a lead may adjust a contact point and a position of an electrode of the lead according to a change in physical position by changing the contact point and the position of the electrode of the lead through external control. This simple orthodontic procedure may eliminate the need for complicated reoperation, thereby reducing the burden on the patient and increasing the satisfaction with the treatment.

DETAILED DESCRIPTION OF THE INVENTION

Hereinafter, embodiments of the present invention will be described with reference to the drawings. In the following description, an example in which a lead of the present invention and a lead system using the lead are applied to a deep brain stimulator for applying electrical stimulation to the deep brain will be described. However, a description of a well-known technical configuration in relation to the deep brain stimulator will be omitted.

For example, descriptions of a configuration/structure/method of a device or system commonly used in deep brain stimulation, such as a structure of an implantable pulse generator, a connection structure/method of the implantable pulse generator and a lead, and a process for transmitting and receiving electrical signals measured through the lead with an external device, will be omitted. Even if these descriptions are omitted, one of ordinary skill in the art will be able to easily understand the characteristic configuration of the present invention through the following description.

Figure 1:
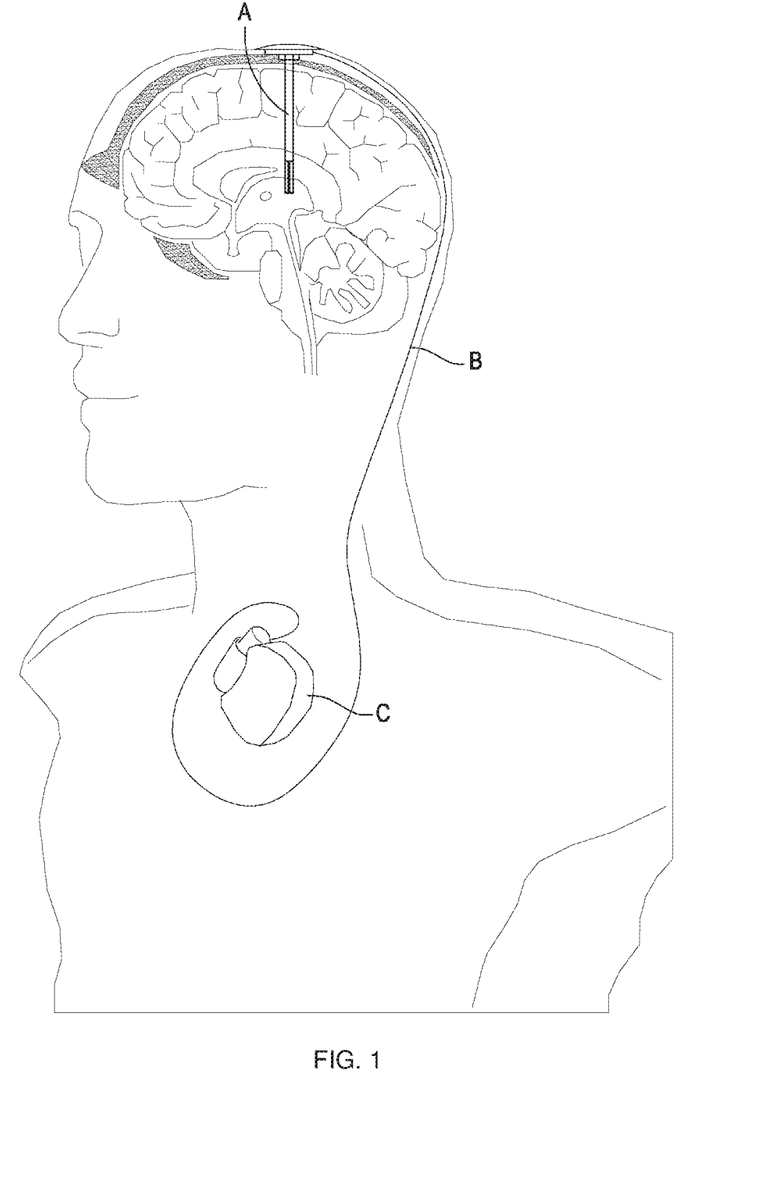
FIG. 1 schematically shows a state in which a deep brain stimulator is applied to the body according to the present invention.

FIG. 1 schematically shows a state in which a deep brain stimulator is applied to the body. As shown, the deep brain stimulator includes a plurality of leads A (only one is shown in FIG. 1) implanted in a specific region of the brain, an implantable pulse generator C implanted subcutaneously in the chest, and an extension connecting the leads to the implantable pulse generator.

When stimulation is generated through the implantable pulse generator, the stimulation is transmitted to a lead through the extension, and micro-electrical stimulation may be applied to a specific region of the brain through the lead.

The following embodiment relates to a lead system for a deep brain stimulator that enables implantation of a lead A from among components of the deep brain stimulator in a specific target region of the brain accurately and with a simple procedure, and a lead.

Figure 2A:
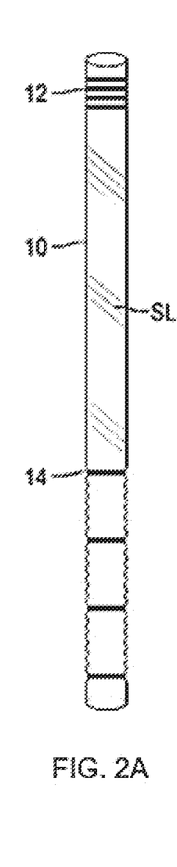
FIGS. 2A, 2B and 2C schematically show various shapes of a lead for a deep brain stimulator according to an embodiment of the present invention.
Figure 2B:
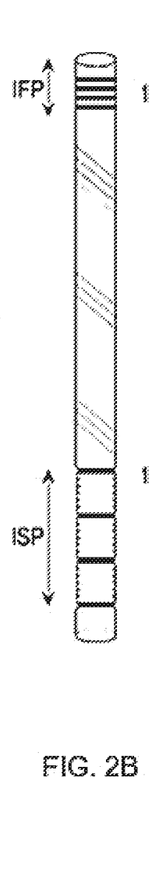
Figure 2C:
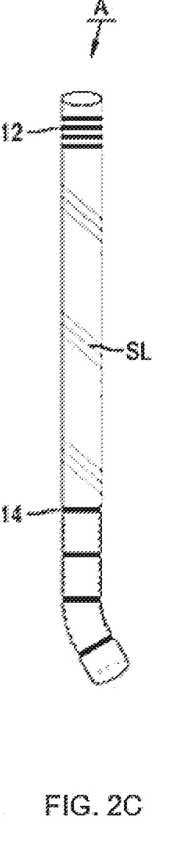

FIGS. 2A, 2B and 2C schematically show various shapes in which a lead for a deep brain stimulator according to an embodiment of the present invention is changed according to operation of a moving plate, a first moving plate and a second moving plate provided in an interface portion IFP and an insertion portion ISP of the electrode wire, and a coupling mode thereof by a wire.

Various states of the lead A are shown in an upper portion of FIGS. 2A, 2B and 2C. As shown, the lead A of the present embodiment includes a lead 10 transmitting a stimulation signal from a brain region into which a lead is inserted, a second electrode 12 provided on the interface portion IFP serving as a connecting portion with an external device as an upper portion of the electrode wire (right side of the drawing), a first electrode 14 provided in the insertion portion ISP to be inserted into the brain region as a lower portion of the electrode wire (left side of the drawing), and a signal line SL provided in a diagonal shape between the interface portion IFP and the insertion portion ISP and interconnecting the first and second electrodes 14 and 12 provided in the insertion portion ISP and the interface portion IFP.

Although not specifically shown, a guide wire is provided which is inserted into an inner space of the electrode wire and supports the electrode wire when the electrode wire is inserted. The guide wire has high rigidity, allowing a lead to be inserted into the body without bending when the lead is inserted, and is removed after the lead is inserted.

As shown in FIGS. 2A, 2B and 2C, the signal line SL is wound and fixed to the outside of the electrode wire in a spiral form, but the present invention is not particularly limited to the shape of the signal line.

In other words, as long as the signal line is connected to electrodes provided at upper and lower ends of the electrode wire, the signal line is not limited to a shape fixed to a surface of the electrode wire 10 spirally, and may be fixedly inserted into the electrode wire 10 spirally. The electrode wire 10 is flexible and has excellent durability, and is formed of a material harmless to the human body, for example, polyurethane.

On the other hand, as shown in the drawing, the insertion portion ISP of the lead in the present embodiment has a structure that is stretchable and bendable, unlike the conventional lead.

Figure 4:
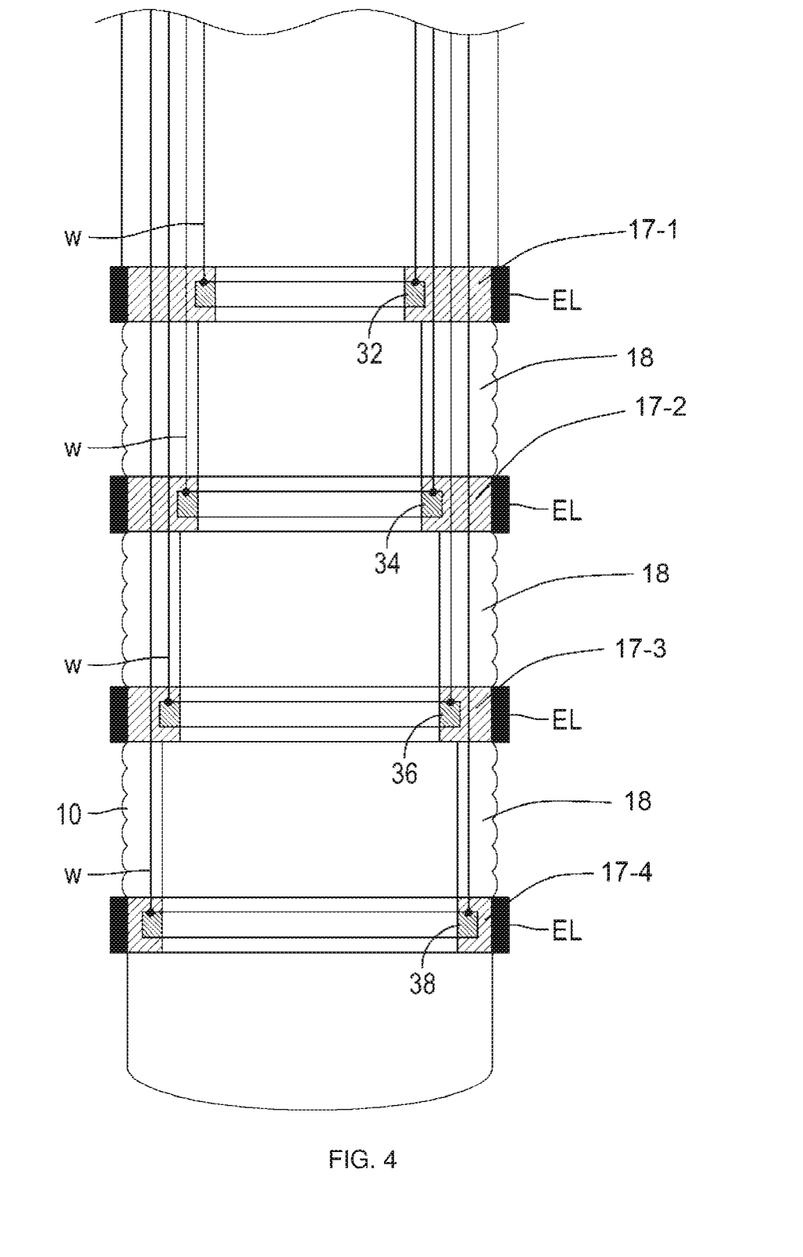
FIG. 4 schematically shows an outline of an internal structure of an insertion portion of an electrode wire and a binding aspect of a fixing plate attached to the insertion portion according to an embodiment of the present invention.

Referring to FIG. 4 showing a cross-sectional structure of the insertion portion ISP, the electrode wire 10 is not composed of a single material in the insertion portion ISP, but has a structure in which a support portion 17 having rigidity and a stretchable portion 18 having elasticity are alternately provided.

That is, a plurality of support portions 17-1 to 17-4 made of a rigid material that has rigidity and is not bent are provided to be apart from each other, and the stretchable portion 18 made of a stretchable material is provided between the plurality of support portions, wherein the support portions 17-1 to 17-4 are fixed to each other to form an integral body. The first electrode 14 is provided on an outer surface of each support portion 17.

The support portions 17-1 to 17-4 have different inner diameters, and fixing plates 32, 34, 36, and 38 of different diameters are fixed to inner surfaces thereof, respectively, and an end of an operation wire W for adjusting the position of the support portion 17 by pushing or pulling a fixing plate is coupled to each fixing plate.

A plurality of operation wires W are apart from one of the fixing plates 32 to 38 in a circumferential direction and are coupled to each other and have sufficient rigidity, and thus, by pushing and pulling the operation wire W, the support portion 17 is pushed or pulled to be inclined.

The operation wire coupled to each of the fixing plates 32 to 38 extends toward the interface portion IFP of the electrode wire 10 through the other fixing plate.

Figure 3:
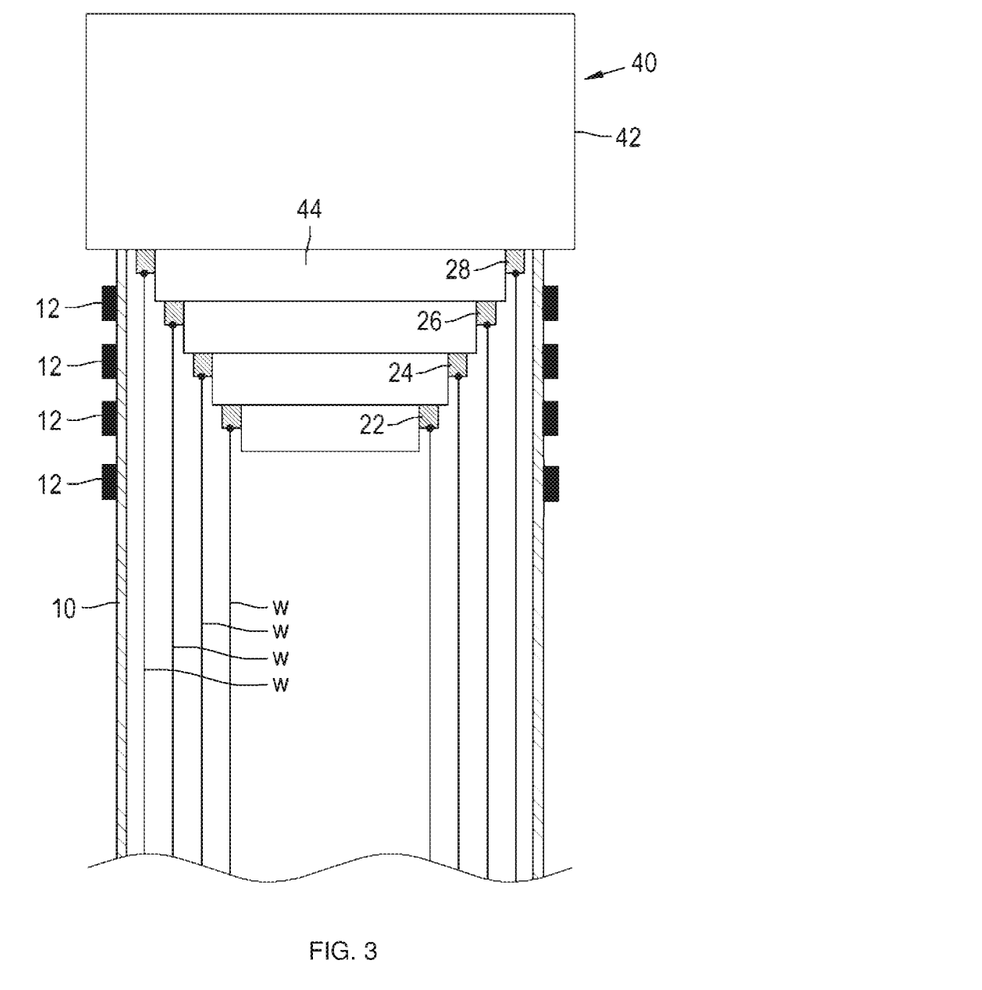
FIG. 3 schematically shows an aspect of a position of a moving plate attached to an actuator and an aspect of a position in an electrode wire according to the present invention.

Referring to FIG. 3, a plurality of moving plates 22, 24, 26, and 28 to which the operation wire W penetrates and is coupled are provided on the interface portion IFP side of the electrode wire 10.

The moving plates 22 to 28 are arranged in contact with an actuator 44. The actuator 44 is formed in multiple stages, one moving plate is arranged at each of the multiple stages, and each stage is linearly driven to move the moving plate up and down.

Accordingly, the operation wire W acts to push and pull, and moves the fixing plates 32 to 38 and the support portions 17 to which the fixing plates are respectively coupled.

The moving plates 22 to 28 are formed with different diameters to correspond to the fixing plates 32 to 38, respectively, and thus, the moving plates 22 to 28 do not interfere with each other and operation wires coupled thereto do not interfere with each other.

The operation wire W extends inside a controller 40 through the moving plates 22 to 28 and may be pulled or pushed by a motor built in the controller 40.

Although not specifically shown in the drawing, the operation wire W penetrates the moving plates 22 to 28 to extend into the controller 40 and is coupled to the motor to operate.

The operation wires W are selectively fixed or released to/from the moving plates 22 to 28. When the operation wires W are fixed to the moving plates 22 to 28, the support portion 17 of the electrode wire is moved by moving of the moving plates 22 to 28, and when the operation wires W are not fixed to the moving plate, each is operated by the motor inside the controller 40.

The fixing and releasing of the operation wires W and the moving plates 22 to 28 may be made simply by hand by a bolt inserted into the moving plates and arranged to press the operation wires W.

Figure 2D:
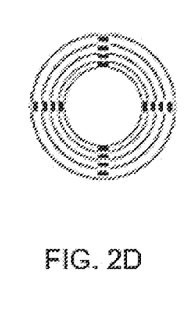
FIGS. 2D, 2E and 2F schematically show a top view, a bottom view and a side view, respectively, of a lead for a deep brain stimulator according to an embodiment of the present invention.
Figure 2E:
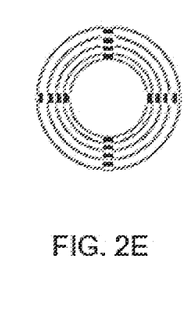
Figure 2F:
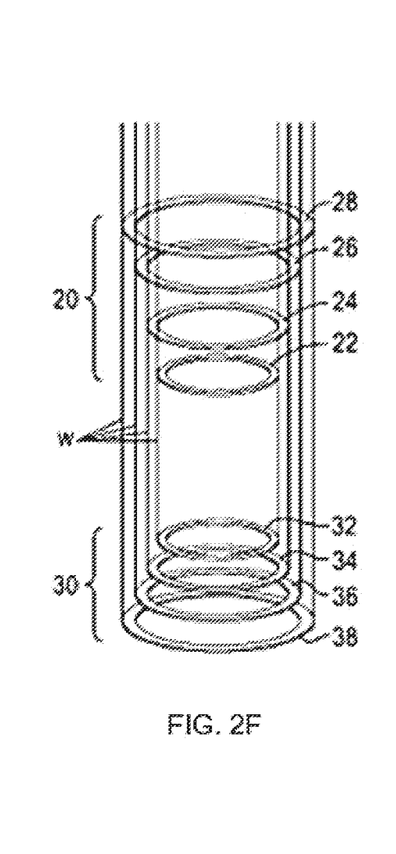

As shown in FIGS. 2D, 2E and 2F, the fixing plates 32 to 38 and the moving plates 22 to 28 form a one-to-one set with each other, and are connected to each other by four operation wires W. With this configuration, by an action of driving each of the moving plates 22 to 28 by the actuator 44 or pushing and pulling the operation wire W by the built-in motor of the controller 40, positions and postures of the fixing plates 32 to 38 coupled to an end of the operation wire W and the support portions 17 coupled to the fixing plates 32 to 38 are adjusted.

Such an operation will be described with reference to FIGS. 5A, 5B, 5C, 5D, 5E and 5F.

Figure 5A:
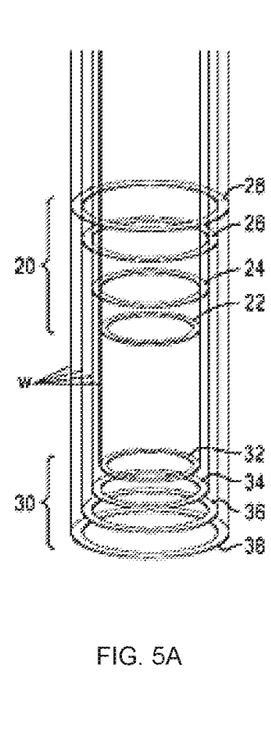
FIGS. 5A, 5B, 5C, 5D, 5E and 5F schematically show the form of a corresponding electrode wire with a position of a moving plate and a fixing plate (FIGS. 5A,5B), and indicate the formation of an insertion portion of the electrode wire according to the movement of the moving plate and fixing plate (FIGS. 5C, 5D, 5E, 5F) according to an embodiment of the present invention.
Figure 5B:
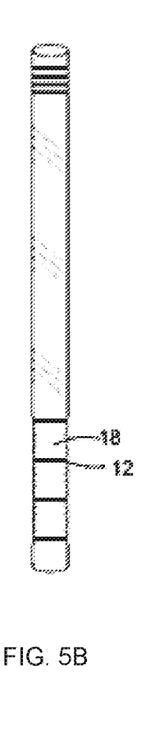

In an example shown in FIGS. 5A and 5B, when the actuator 44 is operated to push each operation wire W, the fixing plates 32 to 38 coupled to the end of the operation wire move downward.

Accordingly, as the support portion 17 is pulled down, the stretchable portion 18 between the support portions is extended to widen a gap between electrodes attached to the support portion 17.

Figure 5C:
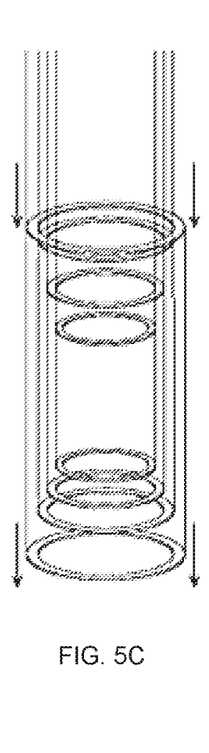
Figure 5D:
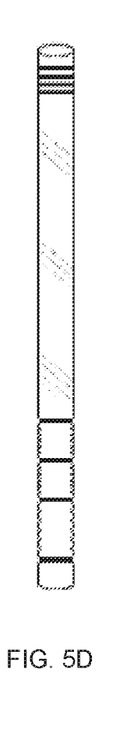

Conversely, as in an example shown in FIGS. 5C and 5D, when only the upper moving plate 28 is pushed from among the moving plates, the lower fixing plate 38 coupled to the upper moving plate 28 by the operation wire is pushed down and the lower support portion 17 coupled to the lower fixing plate 38 moves downward.

In this way, positions and intervals of first electrodes EL attached to the support portion 17 may be adjusted by widening or narrowing the support portions 17 from each other or by moving only a specific support portion 17.

Figure 5E:
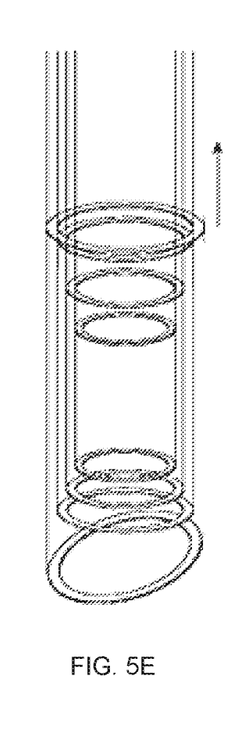
Figure 5F:
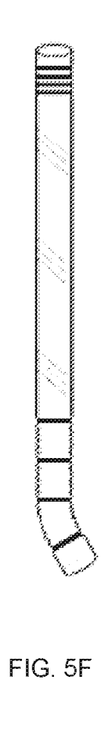

As shown in FIGS. 5E and 5F, the electrode wire 10 may be bent if necessary.

When bending the electrode wire 10, a fastening state between the moving plates 22 to 28 and the operation wire W is released, and the operation wire W is operated by the motor of the controller 40.

A fixing plate is tilted by the action of pulling or pushing only some of operation wires coupled to any one of the fixing plates 32 to 38, and accordingly, the electrode wire is bent as the support portion 17 is inclined.

On the other hand, in the present embodiment, although the moving plates 22 to 28 are used, all of the above-described operations may be implemented by driving each operation wire by a motor built into a controller without using a moving plate.

In addition, when using only an actuator driven in multiple stages without using a built-in motor, a bending action of an electrode wire cannot be implemented, but stretching and adjusting a gap between electrodes may be implemented simply.

By adjusting a position of an electrode and bending an electrode wire, an operator may arrange an electrode in the brain of the recipient at a target position by adjusting a position of the first electrode 14 attached to each support portion 17.

A system including the lead of the above embodiment includes the lead A having the above-described configuration and action, the controller 40, a main processor in charge of communication and control, and an electrode clamp for electrical connection with an electrode of the lead.

The main processor is connected to a separate external device (PC, tablet, smartphone, etc.) to exchange signals, digitizes an electrical signal measured by an electrode, transmits the electrical signal to the external device, or receives a control signal from the external device to drive a motor. The electrode clamp has a semicircular structure attached to an end of a clamp with a spring so that electrode clamp may be well attached to a surface of a lead. In the electrode clamp, the lead comes out of a contact point located on one arm of the clamp and is connected to the main processor, and a guide line is attached to the opposite arm to align positions of the lead and the clamp. Because the main processor and the electrode clamp are known components commonly used in the field of deep brain stimulation, a description thereof will be omitted herein.

Hereinafter, a specific embodiment of implanting a lead using the lead configured as described above will be described.

First, a deep brain stimulation operator (hereinafter referred to simply as 'operator') applies power to a lead system for a deep brain stimulator (not shown) and performs an initialization process (communication connection with an external device for control, and zero adjustment of a moving plate). Next, the operator inserts the electrode wire 10 into a specific region of the brain according to a conventional lead insertion sequence. Next, the operator removes the guide wire, arranges the controller 40 to which the actuator 44 is coupled to fit a hollow hole of the lead A, and then mounts a moving plate to a corresponding portion of a moving plate connector, and connects one end of a wire to the controller. Next, the operator connects the controller to a control unit (not shown) of a lead implantation system for a deep brain stimulator.

On the other hand, the operator opens an electrode clamp, closes the electrode clamp according to a guide line, and connects an electrode contact of the electrode clamp to the electrode so that the electrode contact is in contact with the electrode in a correct position. This process is performed for a plurality of (e.g., four) leads.

The operator transmits a neural signal obtained by moving the moving plates 22 to 28 and the fixing plates 32 to 38 through the wire W to the control unit in real time, and calculates which point of the electrode is closest to a target.

Next, a motor is driven according to a control signal from the control unit, and the moving plate is moved to adjust stimulation position and interval of a target electrode. In this case, when the moving plate reaches a target point or receives a stop signal, the driving of the motor is stopped, and when an insertion position is misaligned, a stimulation position is corrected by pulling only an operation wire of a specific portion using the motor and bending an electrode portion (see FIGS. 5E and 5F).

The operator repeats this process to finally determine interval and position of an electrode. Next, the operator releases coupling of an operation wire coupled to the actuator, and binds the operation wire to a lead immovably. Next, the operator disconnects the control unit and removes the electrode clamp and actuator.

In the description of the above embodiment, the case of using a lead and a lead system according to the present invention for deep brain stimulation has been described. However, in addition to the above-described embodiment, the lead and lead system according to the present invention may be widely used to relieve pain or treat diseases by applying electrical stimulation to body organs, such as spinal cord stimulation for pain relief, frontal nerve stimulation for dysuria, and vagus nerve stimulation for epilepsy or depression.

In the above, although the present invention has been described with reference to embodiments, it should be understood that the present invention is not limited to the embodiments. That is, the embodiments may be variously modified within the scope of the claims to be described later, and these are within the scope of the present invention.

The invention claimed is:

1. A lead implanted in a body to apply electrical stimulation to body organs, the lead comprising:
    an electrode wire having one end provided as an insertion portion to be inserted into a body and another end provided as an interface portion for connection with an external device to transmit a stimulation signal to body organs into which the lead is inserted;
    a plurality of first electrodes in the insertion portion to transmit electrical stimulation to body organs;
    a plurality of second electrodes on the interface portion to receive electrical stimulation applied from outside; and
    a plurality of signal lines configured to interconnect the first electrodes and the second electrodes, respectively, and transmit the electrical stimulation received by the second electrodes to the first electrodes,
    wherein the insertion portion of the electrode wire comprises a plurality of support portions on which the first electrodes are respectively disposed and a plurality of stretchable portions between the support portions and expandable and contractible,
    and further comprises an operation unit for pushing or pulling each support portion in a longitudinal direction of the electrode wire,
    wherein, by pushing or pulling each support portion, a stretchable portion between the support portions is stretched and contracted to adjust a position of the support portion.

2. The lead of claim 1, wherein one end of a plurality of operation wires is coupled to each support portion as an operation unit and the other end of the operation wires extends to an outside of the lead, and by pushing or pulling the other end of the operation wires, a position of each support portion with respect to the electrode wire is adjusted, or an angle of arrangement of the support portion with respect to an extension direction of the electrode wire is adjusted.

3. The lead of claim 1, wherein a plurality of moving plates each movable in the longitudinal direction of the electrode wire are disposed on the interface portion of the electrode wire, and one end of a plurality of operation wires is coupled to each support portion as an operation unit and another end of the operation wires is coupled to each moving plate, so that each operation wire pushes or pulls each support portion by movement of each moving plate.

4. A lead system implanted in a body to apply electrical stimulation to body organs, the lead system comprising:
    a main processor connected to an external device for communication and control;
    one or more leads implanted in a body to apply electrical stimulation to body organs;

an electrode clamp for electrical connection with a lead; and a controller for controlling a position of transmitting electrical stimulation in the lead, wherein each lead comprises:

an electrode wire having one end provided as an insertion portion to be inserted into a body and another end provided as an interface portion for connection with an external device to transmit a stimulation signal to body organs into which the lead is inserted;

a plurality of first electrodes in the insertion portion to transmit electrical stimulation to body organs;

a plurality of second electrodes on the interface portion to receive electrical stimulation applied from outside; and a plurality of signal lines configured to interconnect the first electrodes and the second electrodes, respectively, and transmit the electrical stimulation received by the second electrodes to the first electrodes, wherein the insertion portion of the electrode wire comprises a plurality of support portions on which the first electrodes are respectively disposed and a plurality of stretchable portions between the support portions and expandable and contractible, and further comprises an operation unit for pushing or pulling each support portion in a longitudinal direction of the electrode wire, wherein, by pushing or pulling each support portion, a stretchable portion between the support portions is stretched and contracted to adjust a position of the support portion.

5. The lead system of claim 4, wherein a plurality of operation wires is coupled as an operation unit to each support portion of the lead, and a position of each support portion with respect to the electrode wire is adjusted by pushing or pulling the operation wires, or an angle of arrangement of the support portion with respect to an extension direction of the electrode wire is adjusted, wherein the controller comprises a motor that pushes or pulls each operation wire of the lead.

6. The lead system of claim 4, wherein a plurality of moving plates each movable in the longitudinal direction of the electrode wire are disposed on the interface portion of the electrode wire, and one end of a plurality of operation wires is coupled to each support portion as an operation unit and another end of the operation wires is coupled to each moving plate, so that each operation wire pushes or pulls each support portion by movement of each moving plate, wherein the controller is provided with an actuator coupled with each moving plate of the lead to move the moving plate.

* * * * *